United States Patent [19]

Lang

[11] Patent Number: 5,378,721
[45] Date of Patent: Jan. 3, 1995

[54] HETEROARYLMETHYLBENZENES

[75] Inventor: Marc Lang, Mulhouse, France

[73] Assignee: Ciba-Geigy Corporation, Ardsley, N.Y.

[21] Appl. No.: 82,000

[22] Filed: Jun. 24, 1993

Related U.S. Application Data

[62] Division of Ser. No. 761,103, Sep. 17, 1991, Pat. No. 5,246,952.

[30] Foreign Application Priority Data

Sep. 18, 1990 [CH] Switzerland ............. 03014/90-0

[51] Int. Cl.$^6$ .................... C07D 263/32; A61K 31/42
[52] U.S. Cl. .................. 514/374; 514/378; 548/236; 548/247
[58] Field of Search .......... 548/336, 247; 514/374, 514/372

[56] References Cited

U.S. PATENT DOCUMENTS

| | | | |
|---|---|---|---|
| 3,407,210 | 10/1968 | Schoetensack et al. | 514/365 |
| 3,686,188 | 8/1972 | Huebner et al. | 514/365 |
| 4,268,678 | 5/1981 | Diana et al. | 514/365 |
| 4,452,986 | 6/1981 | Johnson et al. | 514/365 |
| 4,894,381 | 4/1983 | Lang et al. | 514/365 |
| 4,916,144 | 4/1990 | Strchike et al. | 514/365 |
| 4,978,761 | 12/1990 | Goto et al. | 514/365 |
| 5,021,444 | 6/1991 | Trada et al. | 514/365 |
| 5,071,861 | 12/1991 | Bowman | 514/365 |
| 5,073,574 | 12/1991 | Lang | 514/365 |
| 5,098,911 | 3/1992 | Ibrahim | 514/365 |
| 5,112,845 | 5/1992 | Bowman et al. | 514/365 |
| 5,206,256 | 4/1993 | Lang | 514/365 |

FOREIGN PATENT DOCUMENTS

| | | |
|---|---|---|
| 4392389 | 5/1990 | Australia . |
| 0054233 | 6/1982 | European Pat. Off. . |
| 0073663 | 3/1983 | European Pat. Off. . |
| 0165780 | 12/1985 | European Pat. Off. . |
| 0165783 | 12/1985 | European Pat. Off. . |
| 0165784 | 12/1985 | European Pat. Off. . |
| 0207563 | 1/1987 | European Pat. Off. . |
| 0277384 | 8/1988 | European Pat. Off. . |
| 0293978 | 12/1988 | European Pat. Off. . |
| 0296749 | 12/1988 | European Pat. Off. . |
| 0316097 | 5/1989 | European Pat. Off. . |

OTHER PUBLICATIONS

Jones et al. "Estrogen Synthetase Inhibitors 2' Comparison of the Vitro Aromatese Inhibitory Activity for a Variety of Nitrogen Heterocycles Substituted with Diarylmethane or Diarylmethanol Groups" J. Med. Chem. 1990; 33; 416–429.

Katritzky et al. "The Preparation and Fungicidal Activity of a Series of Thiazolyl-and Isothiazolyl-diaryl-carbinols" Can. J. Chem 1988; 66 1617–24.

Ashton et al. "Heterocyclic Analogues of Chlorcylizine with Potent Hypolepidemic Activity" J. Med. Chem. 1984:27: 1245–53.

Fiona et al. "NgN–Dimethyl-N'(thioformyl) Formamidine: Preparation and Properties" Chem Abstract 101:90383h (1984).

Layton et al. "Isothiazoles Part XI' Carbinols, Aryl Ketones, and Aminomethyl Derivatives of Isothiazoles" J. Chem. Soc. (c) 1968: 611–613.

Cross et al. "Selective Thromboxane Synthetase Inhibitors. 4.2–(1H–Imidazol-1-y/methyl Carboxylic Acids of Benzo [6]Juran, Benzo[6]thiophene, Indole, and Naphthalene" J. Med. Chem. vol. 29:1643–1650 (1986).

*Primary Examiner*—Robert Gerstl
*Attorney, Agent, or Firm*—Irving M. Fishman; Karen G. Kaiser

[57] ABSTRACT

Compounds of formula I

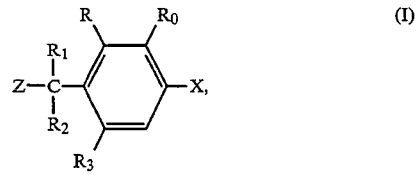

wherein Z, X, R, $R_0$, $R_1$, $R_2$ and $R_3$ are as defined in the description, have valuable pharmaceutical properties and are effective especially against tumors. They are prepared in a manner known per se.

6 Claims, No Drawings

HETEROARYLMETHYLBENZENES

This is a division of Ser. No. 07/761,103 filed Sep. 17, 1991, now U.S. Pat. No. 5,246,952.

The invention relates to compounds of formula I

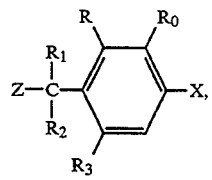

wherein Z is a five-membered nitrogen-containing heteroaromatic ring of the formula

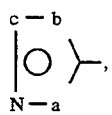

wherein one of the ring atoms a, b and c is oxygen or sulfur and either both of the other two ring atoms a, b and c are CH, or one is CH and the other is nitrogen; R and $R_0$, independently of one another, are hydrogen or lower alkyl; or R and $R_0$ together are a benzo group that is unsubstituted or substituted as indicated below for aryl; $R_1$ is hydrogen, lower alkyl, hydroxy or halogen; $R_3$ is hydrogen; $R_2$ is hydrogen, lower alkyl or aryl; or $R_1$ and $R_2$ together are lower alkylidene; or $R_2$ and $R_3$ together are —$(CH_2)_2$— or —$(CH_2)_3$—; or $R_1$ and $R_2$ and $R_3$ together are a group =CH—$CH_2$— or =CH—$(CH_2)_2$— wherein the single bond in each case is linked to the benzene ring; X is cyano, carbamoyl, N-lower alkylcarbamoyl, N,N-di-lower alkylcarbamoyl, N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl or N-hydroxycarbamoyl; and X may also be halogen, hydroxy, lower alkoxy, aryl-lower alkoxy or aryloxy when $R_2$ and $R_3$ together are —$(CH_2)_2$— or —$(CH_2)_3$— or $R_1$ and $R_2$ and $R_3$ together are a group =CH—$CH_2$— or =CH—$(CH_2)_2$—; wherein aryl is phenyl that is unsubstituted or substituted by one or more substituents from the group consisting of lower alkyl, cycloalkyl, lower alkoxy, hydroxy, lower alkanoyloxy, nitro, amino, lower alkylamino, di-lower alkylamino, halogen, trifluoromethyl, carboxy, lower alkoxycarbonyl, carbamoyl, N-lower alkylcarbamoyl, N,N-di-lower alkylcarbamoyl, N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, cyano; N-phenyl-lower alkylcarbamoyl, N-phenylcarbamoyl, phenyl-lower alkoxy and phenoxy, each of the phenyl groups in the last four substituents mentioned being unsubstituted or substituted by lower alkyl, lower alkoxy, hydroxy, halogen or by trifluoromethyl; and to salts thereof, to processes for the preparation of those compounds, to pharmaceutical compositions comprising those compounds, and to the use of those compounds for the therapeutic treatment of the human or animal body or for the preparation of pharmaceutical compositions.

The compounds of formula I that comprise an asymmetric carbon atom can be in the form of a racemate or of an R- or an S-enantiomer. The invention relates to all those forms and, for example, also to diastereoisomers and mixtures thereof that can occur when there are two or more asymmetric centres in the molecule, and to geometric isomers, for example cis- and trans-isomers, if the molecule comprises a double bond.

Within the context of the present Application, the general terms used hereinbefore and hereinafter have preferably the following meanings:

A five-membered nitrogen-containing heteroaromatic ring of the formula

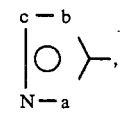

wherein one of the ring atoms a, b and c is oxygen or sulfur and either both of the other two ring atoms a, b and c are CH, or one is CH and the other is nitrogen, includes, especially, the radicals 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl).

The prefix "lower" denotes a radical having up to and including 7, especially up to and including 4, and more especially 1 or 2, carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

Cycloalkyl is preferably $C_3$-$C_8$- and especially $C_3$- or $C_5$-$C_6$-cycloalkyl, which means that it comprises from 3 to 8, and 3, 5 or 6, ring carbon atoms, respectively.

Lower alkylidene is, for example, methylidene (=$CH_2$) or ethylidene.

If R and $R_0$ together are a benzo group, then together with the benzene ring they form a naphthalene structure.

If $R_2$ and $R_3$ together are —$(CH_2)_2$— or —$(CH_2)_3$—, then together with the central carbon atom and the benzene ring those radicals form an indane or a tetraline structure, respectively.

If $R_1$ and $R_2$ and $R_3$ together are a group =CH—$CH_2$— or =CH—$(CH_2)_2$—, wherein the single bond in each case is linked to the benzene ring, then together with the central carbon atom and the benzene ring those radicals form an indene or a 1,2-dihydronaphthalene structure, respectively. The latter can also be referred to as 3,4-dihydronaphthalene—as in the Examples.

Halogen is especially chlorine and bromine, but may also be fluorine or iodine.

Halogen as a definition of $R_1$ is especially fluorine or chlorine, especially fluorine.

Carbamoyl is the group —$CONH_2$.

Lower alkanoyloxy is, for example, formyloxy, acetoxy, propionyloxy, n-butyryloxy, pivaloyloxy or valeroyloxy.

Substituted phenyl is preferably mono- or disubstituted and, especially, monosubstituted.

Aryl as a definition of $R_2$ is especially phenyl that is unsubstituted or substituted by lower alkyl, lower alkoxy, hydroxy, halogen, trifluoromethyl or by cyano, and is, especially, cyanophenyl.

Aryl in general is preferably phenyl that is unsubstituted or substituted by lower alkyl, lower alkoxy, hydroxy, halogen or by trifluoromethyl, and is, especially, phenyl.

Salts of compounds according to the invention are especially pharmaceutically acceptable non-toxic salts. For example, compounds of formula I having basic groups can form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or with amino acids, such as arginine or lysine. Compounds of formula I having an acidic group, for example carboxy, form, for example, metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis(2-hydroxyethyl)amine or tris(2-hydroxyethyl)amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or benzyl-$\beta$-phenethylamine. Compounds of formula I having an acidic and a basic group can also be in the form of internal salts, that is to say, in zwitterionic form.

For isolation or purification it is also possible to use pharmaceutically unacceptable salts, for example picrates or perchlorates. Only the pharmaceutically acceptable, non-toxic salts are used for therapeutic purposes and those are therefore preferred.

The compounds of formula I according to the invention have valuable, especially pharmacological, properties. In particular, they inhibit selectively the enzyme aromatase in mammals including humans. That results in inhibition of the metabolic conversion of androgens into oestrogens. The compounds of formula I are therefore suitable, for example, for the treatment of oestrogen-dependent disorders, including oestrogen-dependent breast cancer, especially in post-menopausal women. In addition, they can be used, for example, in the treatment of gynaecomastia, that is to say, the development of breasts in men, because the aromatisation of steroids is inhibited.

These effects can be demonstrated by in vitro or in vivo tests, preferably in mammals, for example guinea pigs, mice, rats, cats, dogs or monkeys. The dose used is, for example, in a range of approximately from 0.001 to 10 mg/kg, preferably from 0.001 to 1 mg/kg.

The in vitro inhibition of aromatase activity can be demonstrated, for example, using the method described in J. Biol. Chem. 249, 5364 (1974). In addition, $IC_5$ values for aromatase inhibition can be obtained, for example, in vitro from enzyme-kinetic studies relating to the inhibition of the conversion of 4—$^{14}$C-androstenedione into 4—$^{14}$C-oestrone in human placental microsomes. The minimum $IC_{50}$ values for the compounds of the invention are approximately $10^{-9}$M.

In vivo, the inhibition of aromatase can be demonstrated, for example, by the suppression of ovarian oestrogen in female rats which are first injected with mare serum gonadotropin and, 2 days later, with human chorionic gonadotropin, and then on the following day are treated p.o. with a compound of the invention and one hour later with androstenedione. A further possible method of in vivo determination of aromatase inhibition is as follows: androstenedione (30 mg/kg subcutaneously) is administered on its own or together with a compound of the invention (orally or subcutaneously) for 4 days to sexually immature female rats. After the fourth administration the rats are sacrificed and the uteri are isolated and weighed. The aromatase inhibition is determined by the extent to which the uterus hypertrophy caused by the administration of androstenedione on its own is suppressed or reduced by simultaneous administration of the compound of the invention. The minimum effective dose of the compounds of the invention in the in vivo tests is approximately from 0.001 to 1 mg/kg.

The anti-tumour activity, especially in the case of oestrogen-dependent tumours, can be demonstrated in vivo, for example in the case of DMBA-induced mammary tumours in female Sprague-Dawley rats [see Proc. Soc. Exp. Biol. Med. 160, 296–301 (1979)]. The administration of compounds of the invention effects a regression of the tumours, and, furthermore, suppresses the occurrence of new tumours, at daily doses of approximately 1 mg/kg p.o. and above.

In addition, the compounds of formula I do not have an inhibiting effect on the cleavage of the cholesterol side chain and do not induce adrenal hypertrophy; this can be demonstrated by endocrine organ investigations.

Owing to this pharmacological properties as extremely selective inhibitors of the enzyme aromatase, the compounds of formula I are suitable, for example, for the treatment of oestrogen-dependent disorders, such as breast tumours (breast carcinomas), endometriosis, premature labour or endometrial tumours in women or gynaecomastia in men.

The invention relates preferably to compounds of formula I wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl), 5-(1,2,3-thiadiazolyl), 3-(1,2,5-thiadiazolyl), 3-(1,2,5-oxadiazolyl), 4-isothiazolyl, 4-isoxazolyl, 4-(1,2,3-thiadiazo 4-(1,2,3oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, lower alkyl, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; X is cyano; and X may also be halogen when $R_2$ and $R_3$ together are —$(CH_2)_3$— or $R_1$ and $R_2$ and $R_3$ together are a group =CH—$(CH_2)_2$—; and salts thereof.

The invention relates especially to compounds of formula I wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4- isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R, $R_0$ and $R_3$ are hydrogen; $R_1$ is hydrogen, methyl, hydroxy or fluorine; $R_2$ is hydrogen, lower alkyl or cyanophenyl; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; X is cyano; and X may also be halogen when $R_2$ and $R_3$ together are —$(CH_2)_3$— or $R_1$ and $R_2$ and $R_3$ together are a group =CH—$(CH_2)_2$—; and salts thereof.

The invention relates more especially to compounds of formula I wherein Z is 5-isothiazolyl or 5-thiazolyl; R, $R_0$ and $R_3$ are hydrogen; $R_1$ is hydrogen, methyl, hydroxy or fluorine; $R_2$ is hydrogen, lower alkyl or cyanophenyl; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; and X is cyano; and salts thereof.

The invention relates especially to compounds of formula I wherein Z is 5-isothiazolyl or 5-thiazolyl; R, $R_0$ and $R_3$ are hydrogen; $R_1$ is hydrogen, hydroxy or fluorine; $R_2$ is hydrogen, lower alkyl or cyanophenyl; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; and X is cyano; and salts thereof.

As subgroups of a group of compounds of formula I prominence is to be given to: (a) compounds of formula I wherein $R_1$ is hydrogen, methyl, hydroxy or fluorine; (b) compounds of formula I wherein $R_1$ is hydrogen, hydroxy or fluorine; (c) compounds of formula I wherein $R_1$ is hydrogen; (d) compounds of formula I wherein Z is 5-isothiazolyl; (e) compounds of formula I wherein Z is 5-thiazolyl; (f) compounds of formula I wherein $R_2$ is monosubstituted phenyl and the substituent is linked in the 4-position; (g) compounds of formula I wherein $R_2$ is 4-cyanophenyl; and (h) compounds of formula I wherein X is cyano.

The invention relates most especially to the specific compounds described in the Examples and to pharmaceutically acceptable salts thereof.

The compounds of formula I can be prepared in a manner known per se, for example as follows:

(a) for the preparation of a compound of formula I wherein $R_1$ is hydroxy, a compound of formula II

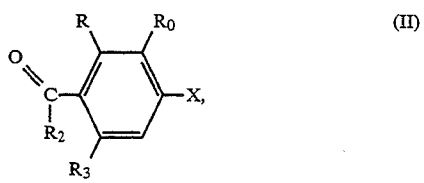

wherein X, R, $R_0$, $R_2$ and $R_3$ are as defined for formula I, is reacted with a compound of formula III

Z—$R_4$ (III), wherein $R_4$ is hydrogen or a protecting group or leaving group attached to a ring carbon atom and Z is as defined for formula I, or (b) for the preparation of a compound of formula I wherein $R_1$ and $R_2$ together are lower alkylidene, a compound of formula IV

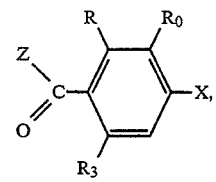

wherein Z. R, $R_0$, $R_3$ and X are as defined for formula I, is reacted with a compound of formula V Alk=$W_1$ (V), wherein Alk is lower alkylidene and $W_1$ is a phosphoranylidene group, or (c) in a compound of formula VI

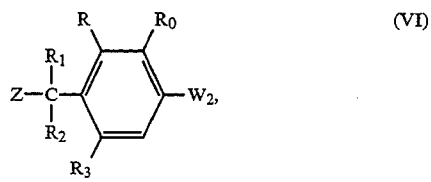

wherein Z, R, $R_0$, $R_1$, $R_2$ and $R_3$ are as defined for formula I and $W_2$ is a group that can be converted into the radical X, $W_2$ is converted into the radical X, a substituent identical to $W_2$ within the group $R_2$ possibly being converted simultaneously, or (d) for the preparation of a compound of formula I wherein $R_1$ is hydrogen, a compound of formula I wherein $R_1$ is hydroxy is reduced, or (e) for the preparation of a compound of formula I wherein $R_1$ and $R_2$ and $R_3$ together are a group =CH—$CH_2$— or =CH—$(CH_2)_2$—, the elements of water are eliminated from a compound of formula I wherein $R_2$ and $R_3$ together are —$(CH_2)$— or —$(CH_2)_3$— and $R_1$ is hydroxy, or (f) for the preparation of a compound of formula I wherein $R_1$ is lower alkyl, a compound of formula I wherein $R_1$ is hydrogen is condensed with a lower alkanol, or with a reactive functional derivative thereof, and/or a resulting compound of formula I is converted into a different compound of formula I, and/or a resulting salt is convened into the free compound or into a different salt, and/or a resulting free compound of formula I is convened into a salt, and/or a resulting mixture of isomeric compounds of formula I is separated into the individual isomers.

In the description of processes (a), (b), (c), (d) and (e) that follows, the symbols Z, R, $R_o$, $R_1$, $R_2$, $R_3$ and X are as defined for formula I, unless otherwise indicated.

Process (a); In a compound of formula III a protecting group or leaving group $R_4$ attached to a ring carbon atom is, for example, tri-lower alkylsilyl. Tri-lower alkylsilyl acts as a protecting group, for example, in 2-trimethylsilylthiazole, where the 2-position of the thiazole is blocked. Tri-lower alkylsilyl acts as a leaving group, for example, in 5-trimethylsilylthiazole, where the linking according to Process (a) takes place in the presence of, for example, caesium fluoride in the 5-position of the thiazole. A further universally acceptable leaving group is, for example, halogen.

In the reaction according to Process (a), normally a compound of formula III wherein $R_4$ is hydrogen or a leaving group is reacted with a base—preferably a strong base—, for example an alkali metal base, for example n-butyllithium, sodium hydride or lithium diisopropylamide (LDA) and then with the ketone or aldehyde of formula II.

In a variant of Process (a), the heteroaromatic compound Z-R$_4$ substituted in the intended linking position by a leaving group R$_4$ is reacted with the aldehyde or ketone of formula II in the presence of an activator, for example caesium fluoride. In that reaction, when an aldehyde of formula II is used, the corresponding acylated heteroaromatic compound is sometimes obtained as secondary product in addition to the desired compound of formula I wherein R$_1$=OH. The acylated heteroaromatic compound is presumably formed as a result of oxidation of the alcohol of formula I which is formed first.

The starting compounds of formulae II and III are known per se or can be prepared analogously to known compounds.

Process (b); In a compound of formula V, a phosphoranylidene group W$_1$ is a radical =P(W$_3$, W$_4$, W$_5$) wherein W$_3$, W$_4$ and W$_5$ may be identical or different and are, for example, lower alkoxy, lower alkyl or aryl. Triphenylphosphine and diethylphosphono may be mentioned by way of example.

Process (b) corresponds to the Wittig reaction and to modifications thereof and is known per se. The starting compounds of formula V are obtained, for example, from the corresponding phosphonium salts of the formula lower alkyl-P(W$_3$, W$_4$, W$_5$)$\oplus$A$\ominus$, wherein A$\ominus$ is an anion, for example a chloride or bromide, by treatment with a base, for example n-butyllithium.

Process (c); In a compound of formula VI a group W$_2$ that can be converted into the radical X is, for example, halogen, amino, carboxy, lower alkoxycarbonyl, halocarbonyl, an acid anhydride, hydroxy, lower alkoxy, aryl-lower alkoxy or aryloxy.

W$_2$=halogen, especially bromine, can be converted into cyano, for example by reaction with a cyanising agent, for example copper(I) cyanide. W$_2$=amino can be converted, for example, by means of diazotisation, for example into halogen, cyano or hydroxy. If W$_2$ is carboxy, lower alkoxycarbonyl, halocarbonyl, for example —COCl, or an acid anhydride, those radicals can be converted by reaction with ammonia, or the corresponding primary or secondary amine, into carbamoyl or N-mono- or N,N-di-substituted carbamoyl. The conversion of substituents in aromatic systems in accordance with Process (c) is known per se.

In the case where in a compound of formula VI the group R$_2$ comprises a substituent identical to W$_2$, for example where R$_2$=—C$_6$H$_4$—W$_2$, the latter may be converted simultaneously when Process (c) is carried out.

The starting compounds of formula VI are prepared, for example, by analogy with Processes (a) to (f), a radical W$_2$ being used in the corresponding reactions instead of the radical X.

The compounds of formula VI wherein Z is a five-membered nitrogen-containing heteroaromatic ring selected from the group 5-isothiazolyl, 5-thiazolyl, 5-isoxazolyl. 5-oxazolyl, 5-(1,2,3-thiadiazolyl), 5-(1,2,3-oxadiazolyl), 3-(1,2,5-thiadiazolyl), 3-(1.2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and R$_0$ are hydrogen; or R and R$_0$ together are a benzo group that is unsubstituted or substituted by lower alkyl, lower alkoxy, hydroxy, halogen or by trifluoromethyl; R$_1$ is hydrogen, lower alkyl, hydroxy, chlorine or fluorine; R$_3$ is hydrogen; R$_2$ is hydrogen, lower alkyl or phenyl that is unsubstituted or substituted by lower alkyl, lower alkoxy, hydroxy, halogen, trifluoromethyl, aryl-lower alkoxy or by aryloxy; or R$_1$ and R$_2$ together are methylidene and W$_2$ is halogen, hydroxy, lower alkoxy, aryl-lower alkoxy or aryloxy; wherein aryl in each case is phenyl that is unsubstituted or substituted by lower alkyl, lower alkoxy, hydroxy, halogen or by trifluoromethyl; and salts thereof, have for their part valuable pharmacologically acceptable properties, and the invention therefore relates also to those compounds. They act as aromatase inhibitors in the same way as the compounds of formula I. Their activity is of the same order of magnitude as that of the compounds of formula I (see above). Therefore the mentioned compounds of formula VI can also be used, for example, for the treatment of the disorders indicated above in the case of the compounds of formula I.

The invention therefore relates also to the novel compounds from the above-mentioned group of compounds of formula VI, on the one hand as intermediates for the preparation of the valuable compounds of formula I and on the other as pharmaceutical active ingredients. and to pharmaceutical compositions comprising one of the mentioned compounds of formula VI together with one or more pharmaceutically acceptable carriers. The invention relates also to the use of the mentioned compounds of formula VI (a) for the treatment of disorders that respond to the inhibition of aromatase, and (b) (for the preparation of pharmaceutical compositions) for the treatment of tumours.

Of the compounds of formula VI prominence is to be given especially to the compounds prepared in Examples 5, 6, 7 and 23.

Compounds of formula I can be converted into different compounds of formula I.

For example, in accordance with Process (d), compounds of formula I wherein R$_1$ is hydroxy can be converted by reduction, for example with tin(II) chloride or glacial acetic acid/aqueous hydriodic acid, into compounds of formula I wherein R$_1$ is hydrogen.

Conversely, compounds of formula I wherein R$_1$ is hydrogen can be converted by oxidation, for example with oxygen in a basic medium, into compounds of formula I wherein R$_1$ is hydroxy.

In addition, compounds of formula I wherein R$_1$ is hydrogen can be converted by reaction with a halogenating agent, for example an N-halosuccinimide, for example N-bromo- or N-chloro-succinimide, a sulfuryl halide, for example SO$_2$Cl$_2$, or elemental halogen, for example Cl$_2$ or Br$_2$, into compounds of formula I wherein R$_1$ is halogen.

The following method is especially suitable for introducing R$_1$=fluorine: there is formed from the corresponding compound of formula I wherein R$_1$=H, by treatment with a strong base, for example an alkali metal diisopropylamide, for example lithium, sodium or potassium diisopropylamide, or a hexamethyl disilazide base, for example potassium, sodium or lithium hexamethyl disilazide, or an alkali metal base, for example sec-, tert- or n-butyllithium, the corresponding carbanion, which is reacted with an electrophilic fluorinating agent, for example an N-F-sulfonamide [see, for example, J. Amer. Chem. Soc. 106. 452 (1984) or J. Fluor.

Chem. 46, 297 (1990)], especially N-fluoro-3,3-dimethyl-2,3-dihydro-1,2-1,2-benzothiazole-1,1-dioxide [see Helv. Chim Acta 72, 1248 (1989) and Chimia 44, 120 (1990)].

Examples of other suitable electrophilic fluorinating agents are: N-F-sulfonimides [see, for example, J. Amer. Chem. Soc. 109, 7194 (1987)], N-F-pyridinium derivatives [see, for example. J. Amer. Chem. Soc. 112, 8563 (1990)], especially N-fluoro-2,4,6-trimethylpyridinium-trifluoromethylsulfonate, N-F-perfluoropiperidines [see, for example, Chem. and Industry (London) 1964, 1864], N-F-quinuclidinium salts [see, for example, J. Fluor. Chem. 41,297 (1988) or J. Chem. Soc. Perkin Trans. I 1988, 2805], N-F-pyridones [see, for example, J. Fluor. Chem. 26, 43 (1984)] or N-F-amides or -lactams [see, for example, J. Org. Chem. 55, 3373 (1990)].

It is also possible for compounds of formula I wherein $R_1$ is hydroxy to be converted by reaction with a halogenating agent, for example a thionyl halide, for example $SOCl_2$ or $SOBr_2$, a phosphorus halide, for example $PBr_3$, $PI_3$ or $PCl_5$, or a hydrohalic acid, for example HBr, into compounds of formula I wherein $R_1$ is halogen.

It is possible in addition for compounds of formula I wherein $R_1$ is hydroxy to be converted by reaction with certain fluorinating agents, for example secondary aminosulfur trifluorides, for example piperidino-sulfur trifluoride or diethylamino-sulfur trifluoride ["DAST", see, for example, J. Org. Chem. 40, 574 (1975)], or $SF_4$ (see. for example. Organic Reactions 34, 319, Wiley, New York etc. 1985), for example in the system $SF_4/HF$, into compounds of formula I wherein $R_1$ is fluorine.

In addition, in accordance with Process (e), compounds of formula I wherein $R_2$ and $R_3$ together are —$(CH_2)_2$— or —$(CH_2)_3$— and $R_1$ is hydroxy, can be converted by reaction with an agent that eliminates the elements of water, for example thionyl chloride, into compounds of formula I wherein $R_1$ and $R_2$ and $R_3$ together are a group =CH—$CH_2$— or =CH—$(CH_2)_2$—, respectively.

Furthermore, in accordance with Process (f), compounds of formula I wherein $R_1$ is hydrogen can be converted by reaction with a lower alkanol, or especially a reactive functional derivative thereof, into compounds of formula I wherein $R_1$ is lower alkyl. In that process, the starting compounds ($R_1$=H) are first converted using a strong base, for example a hexamethyl disilazide base, for example sodium, lithium or especially potassium hexamethyl disilazide, or an alkali metal lower alkanolate, for example potassium tert-butoxide, into the corresponding carbanion and are then alkylated, especially with a lower alkyl halide, especially a lower alkyl iodide, for example methyl iodide.

In addition, for example, compounds of formula I wherein X is halogen, especially bromine, can be converted by reaction with hydroxyaryl compounds or corresponding alkali metal salts thereof, for example potassium phenolate, advantageously, for example, in the presence of copper, into different compounds of formula I wherein X is aryloxy.

Furthermore, for example, compounds of formula I wherein X is cyano can be converted by means of partial hydrolysis, for example with potassium carbonate and aqueous $H_2O_2$ solution, into different compounds of formula I wherein X is carbamoyl. On the other hand, for example, compounds of formula I wherein X is carbamoyl or N-lower alkylcarbamoyl can be converted by means of the removal of the elements of water or lower alkanol into compounds of formula I wherein X is cyano.

In the case of the reactions described in the three preceding paragraphs, as already explained in the case of Process (c), an identical substituent X that may be present in the molecule, for example $R_2$=—$C_6H_4$—X, may be converted simultaneously.

Free compounds of formula I having salt-forming properties that are obtainable by the process can be converted in a manner known per se into their salts; compounds having basic properties can be converted, for example, by treatment with acids or suitable derivatives thereof, and compounds having acidic properties can be converted, for example, by treatment with bases or suitable derivatives thereof.

Mixtures of isomers obtainable in accordance with the invention can be separated into the individual isomers in a manner known per se, racemates for example by forming salts with optically pure salt-forming reagents and separating the mixture of diastereoisomers so obtainable, for example by means of fractional crystallisation.

The reactions listed above can be carried out under reaction conditions known per se, in the absence or, customarily, in the presence of solvents or diluents, preferably those that are inert towards the reagents used and that dissolve those reagents, in the absence or presence of catalysts, condensation agents or neutralising agents, depending on the nature of the reaction and/or of the reactants at reduced, normal or elevated temperature, for example in a temperature range from approximately −80° C. to approximately 200° C., preferably from approximately −20° C. to approximately 150° C., for example at the boiling point of the solvent used, under atmospheric pressure or in a closed vessel, if desired under pressure, and/or in an inert atmosphere, for example in a nitrogen atmosphere.

In view of the close relationship between the compounds of formula I in free form and in the form of salts, hereinbefore and hereinafter any reference to the free compounds or their salts should be understood as including the corresponding salts or free compounds, respectively, as appropriate and expedient.

The compounds, including their salts, can also be obtained in the form of hydrates, or their crystals can include, for example, the solvent used for crystallisation.

In the process of the present invention, it is preferable to use those starting materials which result in the compounds described at the beginning as being especially valuable.

The invention relates also to those forms of the process according to which a compound obtainable as intermediate at any stage of the process is used as starting material and the remaining process steps are carried out, or a starting material is formed under the reaction conditions or is used in the form of a derivative, for example a salt thereof.

The present invention relates also to pharmaceutical compositions that comprise as active ingredient one of the pharmacologically active compounds of formula I. Compositions for enteral, especially oral, and for parenteral administration are especially preferred. The compositions comprise the active ingredient on its own or, preferably, together with a pharmaceutically acceptable carrier. The dose of the active ingredient depends upon the disease to be treated, and upon the species, its age, weight and individual condition, and upon the mode of administration.

The pharmaceutical compositions comprise from approximately 0.1% to approximately 95% active ingredient, forms of administration that are in single dose form preferably comprising from approximately 1% to approximately 90%, and forms of administration that are not in single dose form preferably comprising from approximately 0.1% to approximately 20% active ingredient. Unit dose forms, such as dragées, tablets or capsules. comprise from approximately 0.5 mg to approximately 100 mg of active ingredient.

The pharmaceutical compositions of the present invention are prepared in a manner known per se, for example by means of conventional mixing, granulating, confectioning, dissolving or lyophilising processes. For example, pharmaceutical compositions for oral administration can be obtained by combining the active ingredient with one or more solid carriers, optionally granulating a resulting mixture, and processing the mixture or granules, if desired and/or if appropriate, by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients are especially flow conditioners and lubricants, for example silicic acid. talc, stearic acid or salts thereof, such as magnesium or calcium stearate. and/or polyethylene glycol, or derivatives thereof.

Dragée cores may be provided with suitable non-enteric or enteric coatings, there being used, inter alia, concentrated sugar solutions which may contain gum arabic, talc, polyvinylpyrrolidone, polyethylene glycol and/or titanium dioxide, coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical compositions are dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil or liquid polyethylene glycols, to which stabilisers may likewise be added.

Other oral forms of administration are, for example, syrups prepared in customary manner which comprise the active ingredient, for example, in suspended form and in a concentration of approximately from 0.01% to 2%, preferably about 0.1% or in a similar concentration that provides a suitable single dose when administered, for example, in measures of 5 or 10 ml. Also suitable are, for example, powdered or liquid concentrates for the preparation of shakes, for example in milk. Such concentrates may also be packed in single dose quantifies.

There come into consideration as rectally administrable pharmaceutical compositions, for example, suppositories that consist of a combination of the active ingredient and a suppository base. Suitable suppository bases are, for example, natural or synthetic triglycerides, paraffin hydrocarbons, polyethylene glycols or higher alkanols.

Suitable for parenteral administration are especially aqueous solutions of an active ingredient in water-soluble form, for example of a water-soluble salt, or aqueous injection suspensions that comprise viscosity-increasing substances, for example sodium carboxymethylcellulose, sorbitol and/or dextran, and, optionally, stabilisers. The active ingredient, optionally together with excipients, can also be in the form of a lyophilisate and can be made into a solution prior to parenteral administration by the addition of suitable solvents.

Solutions used, for example, for parenteral administration can also be used as infusion solutions.

The invention relates also to a method of treating the pathological conditions mentioned above. The compounds of the present invention can be administered prophylactically or therapeutically, and are preferably administered in the form of pharmaceutical compositions. A daily dose of from approximately 0.5 mg to approximately 100 mg, preferably from approximately 1 mg to approximately 20 mg, of a compound of the present invention will be administered in the case of a body weight of approximately 70 kg.

The following Examples illustrate the present invention; temperatures are given in degrees Celsius. The following abbreviations are used: ether=diethyl ether; ethyl acetate=acetic acid ethyl ester; THF=tetrahydrofuran; hexane=n-hexane; DMSO=dimethyl sulfoxide; DMF=dimethylformamide; TLC=thin-layer chromatography; RT=room temperature.

EXAMPLE 1:
4-[α-(4-Cyanophenyl)-α-hydroxy-5-isothiazolylmethyl]-benzonitrile 0.41 ml of diisopropylamine is dissolved in 5 ml of abs. THF, the solution is cooled to $-75°$, and 1.53 ml of 1.6M n-butyllithium in hexane are added. This solution is added dropwise to a stirred mixture, cooled to $-75°$, of 204 mg of isothiazole in 18 ml of THF. After stirring at $-75°$ for one hour, a solution of 539 mg of 4,4'-dicyanobenzophenone in 5 ml of THF is added to the mixture. After stirring for a further 10 minutes, the cooling bath is removed and, once a temperature of 0° has been reached, the reaction mixture is poured onto 40 ml of an ice-cooled saturated aqueous ammonium chloride solution. The product is extracted several times with ether, and the combined organic extracts, after drying over sodium sulfate, are concentrated. The crude product is purified by column chromatography (SiO$_2$, hexane/ethyl acetate 2:1 ) and crystallised from hexane; m.p. 162°–164°; $^1$H-NMR (CDCl$_3$): δ(ppm)=3.37 (s,1H), 7.0 (d,1H), 7.5 and 7.7 (m,8H), 8.46 (d,1H).

The starting material is prepared as follows:
(a) 4,4'-Dicyanobenzophenone 8.13 g of CuCN are added to a solution of 5.1 g of 4,4'-dibromobenzophenone in 90 ml of DMF, and the mixture is stirred under reflux for 13 hours. After cooling, the reaction mixture is diluted with ethyl acetate, washed twice with 50% aqueous ethylenediamine solution, twice with water and then three times with brine, dried and concentrated. Column chromatography (SiO$_2$, toluene to toluene/ethyl acetate 95:5) yields the crystalline title compound; TLC (toluene/ethyl acetate 9:1): R$_f$=0.34; IR (CH$_2$Cl$_2$): 2220, 1670, 1605, 1405 cm$^{-1}$.

EXAMPLE 2:
4-[α-(4-Cyanophenyl)-5-isothiazolylmethyl]-benzonitrile

Analogously to Example 4, 208 mg of 4-[α-(4-cyanophenyl)-α-hydroxy-5-isothiazolylmethyl]-benzonitrile (Example 1) in 2.38 ml of glacial acetic acid are converted into the title compound using 296 mg of tin(II) chloride and 0.761 ml of 36.5% hydrochloric acid. Purification is carried out by means of column chromatography (SiO$_2$, 0.2 bar, hexane/ethyl acetate 3:1) and crystallisation from hexane; m.p. 95°–98°; $^1$H-NMR (CDCl$_3$): δ(ppm)=5.9 (s, 1H), 6.95 (d, 1H), 7.32 and 7.7 (m,8H), 8.48 (d,1H); IR (CH$_2$Cl$_2$): 2220, 1600 cm$^{-1}$.

EXAMPLE 3:
4-[α-(4-Cyanophenyl)-α-hydroxy-5-thiazolylmethyl]-benzonitrile Analogously to Example 1, the title compound is prepared starting from 0.512 ml of diisopropylamine, 2.44 ml of a 1.6M n-butyllithium solution, 530 mg of 2-trimethylsilylthiazole and 603 mg of 4,4'-dicyanobenzophenone in THF at −70° and with working up in the same manner. Purification by column chromatography (SiO$_2$, hexane/ethyl acetate 2:1) yields the title compound in pure form. TLC (hexane/ethyl acetate 2:1) R$_f$=0.2; $^1$H-NMR (CDCl$_3$): δ(ppm)=4.39 (s,1H), 7.42 (d,1H), 7.54 and 7.7 (m,8H), 7.88 (d,1H).

EXAMPLE 4:
4-[α-(4-Cyanophenyl)-5-thiazolylmethyl]-benzonitrile 235 mg of 4-[α-(4-cyanophenyl)-α-hydroxy-5-thiazolylmethyl]-benzonitrile (Example 3) are dissolved in 2.68 ml of glacial acetic acid, and 334 mg of tin(II) chloride and 0.86 ml of 36.5% hydrochloric acid are added in succession. The yellow solution is stirred for 2 hours at 120° and then ovenight at RT. The colourless reaction mixture is diluted with 9.2 ml of water, and the solid that crystallises out is filtered off with suction and dried at 50° under reduced pressure. It is then dissolved in a small amount of THF and stirred with 0.059 ml of pyridine. After concentration by evaporation, the residue is taken up in ethyl acetate, washed in succession with water, 2N HCl, water and brine, and, after drying over sodium sulfate, is concentrated. Column chromatography (SiO$_2$, hexane/ethyl acetate 1:1) yields the title compound, which is crystallised from ether; m.p. 54°–56°; $^1$H-NMR (CDCl$_3$): δ(ppm)=4.31 (s,1H), 7.42 (d, 1H), 7.53 and 7.68 (m,8H), 7.88 (d,1H).

EXAMPLE 5:
Bis(4.4'-bromophenyl)-(5-isothiazolyl)methanol

Analogously to Example 1, the title compound is prepared starting from 0.34 ml of diisopropylamine, 1.25 ml of a 1.6M n-butyllithium solution, 170 mg of isothiazole and 680 mg of 4,4'-dibromobenzophenone in THF at −75°, with working up in the same manner. The title compound is purified by column chromatography (SiO$_2$ 0.04–0.06 mesh, 0.2 bar, hexane/ethyl acetate 4:1) and crystallised from hexane; m.p. 139°–140°; $^1$H-NMR (CDCl$_3$): δ (ppm)=3.1 (s,1H), 6.99 (d,1H), 7.22 and 7.49 (m,8H), 8.41 (d,1H).

EXAMPLE 6:
Bis(4,4'-bromophenyl)-(5-isothiazolyl)methane

Analogously to Example 4, 170 mg of bis(4,4'-bromophenyl)-(5-isothiazolyl)methanol (Example 5) in 1.45 ml of glacial acetic acid are converted into the title compound with 180 mg of tin(II) chloride and 0.464 ml of 36.5% hydrochloric acid. Working up in the same manner, purification by column chromatography (SiO$_2$, hexane to hexane/ethyl acetate 20:1) and crystallisation several times from hexane yield the pure title compound; m.p. 63°–67°; $^1$H-NMR (CDCl$_3$): δ (ppm)=5.6 (s,1H), 6.92 (d, 1H), 7.07 and 7.48 (m,8H), 8.41 (d,1H).

EXAMPLE 7:
Bis(4,4'-bromophenyl)-(5-thiazolyl)methanol

Analogously to Example 3, the title compound is prepared starting from 0.68 ml of diisopropylamine, 2 ml of 1.6M n-butyllithium solution, 0.63 g of 2-trimethylsilylthiazole, and 1.36 g of 4,4'-dibromobenzophenone in THF at −75°, with working up in the same manner. The title compound is purified by column chromatography (SiO$_2$, 0.1 bar, hexane/ethyl acetate); $^1$H-NMR (CDCl$_3$): δ (ppm)=4.14 (br, 1H), 7.25 and 7.48 (m,8H), 7.36 (d,1H), 7.85 (d,1H).

EXAMPLE 8: (a) 5-(4-Cyanobenzoyl)-thiazole and (b) 4-(α-hydroxy-5-thiazolylmethyl)-benzonitrile 15.7 g of 4-cyanobenzaldehyde and 9.1 g of caesium fluoride are added to a solution of 9.4 g of 5-trimethylsilylthiazole in 0.56 l of THF, and the mixture is heated under reflux for 16 hours. The solid material is filtered off and the solvent is concentrated. Column chromatography (SiO$_2$, hexane/ethyl acetate 1:2) yields first (a) 5-(4-cyanobenzoyl)-thiazole [R$_f$ hexane/ethyl acetate 1:2)=0.65], m.p. (after crystallisation from ethyl acetate) 181°–182°; $^1$H-NMR (CDCl$_3$): δ (ppm)=8.88 and 8 (m,4H), 8.36 (s,1H), 9.14 (s,1H), and then (b)4-(α-hydroxy-5-thiazolylmethyl)-benzonitrile [R$_f$ (hexane/ethyl acetate 1:2)=0.35], m.p. (after crystallisation from toluene) 115°–117°; $^1$H-NMR (CDCl$_3$): δ (ppm)=3.05 (d,1H), 6.2 (d,1H), 7.58 and 7.7 (m,4H), 7.73 (s,1H), 8.78 (s,1H).

EXAMPLE 9: 4-(5-Thiazolylmethyl)-benzonitrile

30 µl of dimethyldichlorosilane are added to a solution of 27 mg of 4-(α-hydroxy-5-thiazolylmethyl)-benzonitrile (Example 8b) and 75 mg of sodium iodide in 0.125 ml of acetonitrile after stirring for one hour at 55°; after a further 8 hours at the same temperature, the mixture is allowed to cool and is diluted with 1.5 ml of ethyl acetate. The organic phase is separated off and then washed in succession with water, twice with saturated sodium hydrogen carbonate solution, with 10 % sodium thiosulfate solution and with brine. After drying over sodium sulfate, the title compound is purified by preparative thin layer chromatography (hexane/ethyl acetate 1:2) [R$_f$ (hexane/ethyl acetate 1:2)=0.52]; $^1$H-NMR (CDCl$_3$): δ (ppm)=4.25 (s,2H), 7.36 and 7.65 (m,4H), 7.68 (s,1H), 8.75 (s,1H).

EXAMPLE 10:
1-(4-Cyanophenyl)-1-(5-thiazolyl)-ethylene 714 mg of methyltriphenylphosphonium bromide are introduced into 6.7 ml of ether, and 0.973 ml of 1.6M n-butyllithium in hexane is added at 7°. The orange suspension is stirred at the same temperature for 1.5 hours and then reacted with a suspension, cooled to 7°, of 5-(4-cyanobenzoyl)-thiazole (Example 8a) in 3 ml of ether. After stirring for 3 hours at RT, the ether is replaced by ethyl acetate and the mixture is stirred for a further 2 hours under reflux. The solid material is filtered off with suction and the mother liquor is concentrated. The residue is taken up in methylene chloride and the organic phase is washed in succession with 7 ml of 2N hydrochloric acid and with water, dried over sodium sulfate and concentrated. The crude product is purified by column chromatography ($SiO_2$ 0.04–0.06 mesh, 0.1 bar, hexane/ethyl acetate 2:1 to 1:1) and crystallised from hexane; m.p. 71°–73°; $^1$H-NMR ($CDCl_3$): δ (ppm)=5.5 (s,1H), 5.73 (s,1H) 7.54 and 7.71 (m,4H), 7.69 (s, 1H), 8.78 (s,1H).

EXAMPLE 11:
1-(4-Cyanophenyl)-1-(5-thiazolyl)-ethanol

Analogously to Example 7, the title compound is obtained starting from 1. 101 g of 2-trimethylsilyl-thiazole, 1.19 ml of diisopropylamine, 4.375 ml of n-butyllithium solution (1.6M in hexane) and 1.016 g of 4-cyanoacetophenone in 84 ml of THF. The crude product is purified by column chromatography ($SiO_2$, 0.2 bar, hexane/ethyl acetate 2:1 ) and subsequent crystallisation from ether; m.p. 162°–164°; $^1$H-NMR ($d_6$-DMSO): δ (ppm)=1.93 (s,3H), 7.0 (s,1H), 7.63 (d, 1H), 7.75 (d,1H), 7.8 (m,4H).

EXAMPLE 12:
6-Chloro-1-hydroxy-1-(5-isothiazolyl)-1,2,3,4-tetrahydronaphthalene Analogously to Example 1, the title compound is obtained starting from 225 mg of isothiazole, 0.51 ml of diisopropylamine, 1.87 ml of 1.6M n-butyllithium in hexane and 540 mg of 6-chloro-1-tetralone in 36 ml of THF. The crude product is purified by column chromatography ($SiO_2$, 0.2 bar, hexane/ethyl acetate 9:1 ). $^1$H-NMR ($CDCl_3$): δ (ppm)=1.9–2.31 (m,4H), 2.17 (s,1H), 2.9 (t,2H), 6.83 (d,1H), 7.17 (m,3H), 8.34 (d,1H).

EXAMPLE 13:
6-Chloro-1-(5-isothiazolyl)-3,4-dihydronaphthalene 0.072 ml of thionyl chloride is added at room temperature to a solution of 132 mg of 6-chloro-1-hydroxy-1-(5-isothiazolyl)-1,2,3,4-tetrahydronaphthalene (Example 12) in 0.45 ml of benzene, and the mixture is then stirred at 75° for 1.5 hours. The mixture is concentrated under reduced pressure, 0.156 ml of morpholine is added to the resulting resin, and the mixture is stirred at 75° for 2.5 hours. The black suspension is cooled to 2° and treated with 5N HCl which has likewise been precooled. The pH is then adjusted to 8 with solid $NaHCO_3$ and extraction is carried out with chloroform. The organic phase is separated off, dried over sodium sulfate and concentrated. The crude title compound is purified by column chromatography ($SiO_2$, hexane/ethyl acetate 4:1 ) and crystallisation from hexane; $^1$H-NMR ($CDCl_3$): δ (ppm)=2.44 (m,2H), 2.85 (m,2H), 6.37 (t,1H), 7.14 (m,2H), 7.19 (d,1H), 7.21 (s,1H), 8.49 (d,1H).

EXAMPLE 14:
6-Bromo-1-(5-isothiazolyl)-3,4-dihydronaphthalene

Analogously to Example 13, the title compound is obtained from 6-bromo- 1-hydroxy-1-(5-isothiazolyl)-1,2,3,4-tetrahydronaphthalene, which is prepared analogously to Example 12.

EXAMPLE 15:
6-Cyano-1-hydroxy-1-(5-isothiazolyl)-1,2,3,4-tetrahydronaphthalene Analogously to Example 12, the crude title compound is obtained starting from 353 mg of isothiazole, 0.632 ml of diisopropylamine, 3 ml of 1.6M n-butyllithium in hexane and 546 mg of 6-cyano-1-tetralone in 38 ml of THF. It is purified by column chromatography ($SiO_2$, hexane/ethyl acetate 4:1) and crystallisation from hexane; m.p. 182°–184°; $^1$H-NMR ($d_6$-DMSO): δ (ppm)=1.76 and 1.97 (2 m,4H), 2.9 (t,2H), 6.65 (s,1H), 6.93 (d,1H), 7.37 (dd,1H), 7.59 (dd,1H), 7.7 (d,1H), 8.39 (d,1H).

EXAMPLE 16:
6-Cyano-1-(5-isothiazolyl)-3,4-dihydronaphthalene

Analogously to Example 13.92 mg of 6-cyano-1-hydroxy-1-(5-isothiazolyl)-1,2,3,4-tetrahydronaphthalene (Example 15) and 0.051 ml of thionyl chloride in 0.32 ml of benzene, with the subsequent addition of 0.112 ml of morpholine, are converted into the crude title compound, which is purified by column chromatography ($SiO_2$, 0.1 bar, hexane/ethyl acetate 4:1) and crystallisation from hexane; m.p. 77°–81°; $^1$H-NMR ($CDCl_3$): δ (ppm)=2.5 (m,2H), 2.92 (t,2H), 6.54 (t,2H), 7.2 (d,1H), 7.29 (d,1H), 7.5 (dd,1H), 7.55 (d,1H), 8.5 (d,1H).

EXAMPLE 17:
6-Chloro-1-hydroxy-1-(5-thiazolyl)-1,2,3,4-tetrahydronaphthalene Analogously to Example 1, the title compound is obtained starting from 472 mg of 2-trimethylsilyl-thiazole, 0.51 ml of diisopropylamine, 1.875 ml of 1.6M n-butyllithium in hexane and 541 mg of 6-chloro-1-tetralone in 36 ml of THF. The crude product is purified by column chromatography ($SiO_2$, 0.1 bar, hexane/ethyl acetate 9:1) and subsequent crystallisation from hexane; m.p. 108°–109°; $^1$H-NMR ($CDCl_3$): δ (ppm)=1.9–2.44 (m,4H), 2.92 (t,2H), 3.49 (s,1H), 7.12 (m,2H), 7.17 (m,1H), 7.31 (d,1H), 7.66 (d,1H).

EXAMPLE 18:
6-Chloro-1-(5-thiazolyl)-3,4-dihydronaphthalene

Analogously to Example 13, the crude title compound is obtained starting from 79.6 mg of 6-chloro-1-hydroxy-1-(5-thiazolyl)-1,2,3,4-tetrahydronaphthalene (Example 17) and 0.043 ml of thionyl chloride in 0.27 ml of benzene, with the subsequent addition of 0.094 ml of morpholine. It is purified by column chromatography twice, $SiO_2$, 0.1 bar, (a) hexane/ethyl acetate 5:1 and (b) hexane/ethyl acetate 12:1; $^1$H-NMR ($CDCl_3$): δ (ppm)=2.48 (m,2H), 2.85 (t,2H), 6.66 (t,1H), 7.18 (m,2H), 7.31 (d,1H), 7.68 (d,1H), 7.88 (d,1H).

EXAMPLE 19: 6-Cyano-1-hydroxy-1-(5-thiazolyl)-1,2,3,4-tetrahydronaphthalene

Analogously to Example 1, the crude title compound is obtained starting from 472 mg of 2-trimethylsilyl-thiazole, 0.51 ml of diisopropylamine, 1.88 ml of 1.6M n-butyllithium in hexane and 513 mg of 6-cyano-1 -tetralone in 36 ml of THF. It is purified by column chromatography ($SiO_2$, 0.2 bar, hexane/ethyl acetate 3:1) and crystallisation from hexane. $^1$H-NMR ($CDCl_3$): δ (ppm)=2.0 (m,2H), 2.25 and 2.42 (2 m,2H), 2.97 (t,2H), 3.73 (s,1H) 7.34 (2 d,2H), 7.42 (dd,1H), 7.5 (d,1H), 7.75 (d,1H); IR (CH$_2$Cl$_2$): 2220 cm$^{-1}$.

EXAMPLE 20:
6-Cyano-1-(5-thiazolyl)-3,4-dihydronaphthalene

Analogously to Example 13, the crude title compound is obtained starting from 192 mg of 6-cyano-1-hydroxy-1-(5-thiazolyl)-1,2,3,4-tetrahydronaphthalene (Example 19) and 0.108 ml of thionyl chloride in 0.67 ml of benzene, with the subsequent addition of 0.235 ml of morpholine. It is purified by column chromatography (SiO$_2$, hexane/ethyl acetate 9:1) and crystallisation from hexane; m.p. 78°–79°; $^1$H-NMR (CDCl$_3$): δ (ppm)=2.51 (m,2H), 2.9 (t,2H), 6.82 (t,1H), 7.34 (d,1H), 7.48 (d,1H), 7.53 (dd,1H), 7.85 (d,1H), 7.92 (d,1H).

EXAMPLE 21: The following compounds can also be prepared analogously to Examples 1 to 20:

(a) 4-[α-(4-cyanophenyl)-5-isoxazolylmethyl]-benzonitrile
(b) 4-[α-(4-cyanophenyl)-5-oxazolylmethyl]-benzonitrile
(c) 4-[α-(4-cyanophenyl)-5-(1,2,3-thiadiazolyl)-methyl]-benzonitrile
(d) 4-[α-(4-cyanophenyl)-5-(1,2,3-oxadiazolyl)-methyl]-benzonitrile
(e) 4-[α-(4-cyanophenyl)-3-(1,2,5-thiadiazolyl)-methyl]-benzonitrile
(f) 4-[α-(4-cyanophenyl)-3-(1,2,5-oxadiazolyl)-methyl]-benzonitrile
(g) 4-[α-(4-cyanophenyl)-4-isothiazolylmethyl]-benzonitrile
(h) 4-[α-(4-cyanophenyl)-4-isoxazolylmethyl]-benzonitrile
(i) 4-[α-(4-cyanophenyl)-4-(1,2,3-thiadiazolyl)-methyl]-benzonitrile
(j) 4-[α-(4-cyanophenyl)-4-(1,2,3-oxadiazolyl)-methyl]-benzonitrile
(k) 4-[α-(4-cyanophenyl)-2-(1,3,4-thiadiazolyl)-methyl]-benzonitrile
(l) 4-[α-(4-cyanophenyl)-2-(1,3,4-oxadiazolyl)-methyl]-benzonitrile
(m) 4-[α-(4-cyanophenyl)-5-(1,2,4-thiadiazolyl)-methyl]-benzonitrile
(n) 4-[α-(4-cyanophenyl)-5-(1,2,4-oxadiazolyl)-methyl]-benzonitrile
(o) 6-cyano-1-(5-isoxazolyl)-3,4-dihydronaphthalene
(p) 6-cyano-1-(5-oxazolyl)-3,4-dihydronaphthalene
(q) 6-cyano-1-[5-(1,2,3-thiadiazolyl)]-3,4-dihydronaphthalene
(r) 6-cyano-1-[5-(1,2,3-oxadiazolyl)]-3,4-dihydronaphthalene
(s) 6-cyano-1-[3-(1,2,5-thiadiazolyl)]-3,4-dihydronaphthalene
(t) 6-cyano-1-[3-(1,2,5-oxadiazolyl)]-3,4-dihydronaphthalene
(u) 6-cyano-1-(4-isothiazolyl)-3,4-dihydronaphthalene
(v) 6-cyano-1-(4-isoxazolyl)-3,4-dihydronaphthalene
(w) 6-cyano-1-[4-(1,2,3-thiadiazolyl)]-3,4-dihydronaphthalene
(x) 6-cyano-1-[4-(1,2,3-oxadiazolyl)]-3,4-dihydronaphthalene
(y) 6-cyano-1-[2-(1,3,4-thiadiazolyl)]-3,4-dihydronaphthalene
(z) 6-cyano-1-[2-(1,3,4-oxadiazolyl)]-3,4-dihydronaphthalene
(aa) 6-cyano-1-[5-(1,2,4-thiadiazolyl)]-3,4-dihydronaphthalene
(ab) 6-cyano-1-[5-(1,2,4-oxadiazolyl)]-3,4-dihydronaphthalene

EXAMPLE 22:
4-[α-(4-Cyanophenyl)-5-isothiazolylmethyl]-benzonitrile

Analogously to Example 1a, 500 mg of bis(4,4'-bromophenyl)-(5-isothiazolyl)methane (Example 6) in DMF are converted using CuCN into the title compound, m.p. 95°–98°.

EXAMPLE 23:
Bis(4,4'-bromophenyl)-(5-thiazolyl)methane

Analogously to Example 4, bis(4,4'-bromophenyl)-(5-thiazolyl)methanol (Example 7) is converted into the title compound in glacial acetic acid using tin(II) chloride and 36.5% hydrochloric acid.

EXAMPLE 24:
4-[α-(4-Cyanophenyl)-5-thiazolylmethyl]-benzonitrile

Analogously to Example 1a, bis(4,4'-bromophenyl)-(5-thiazolyl)methane (Example 23) is converted in DMF with CuCN into the title compound. m.p. 54°–56°.

EXAMPLE 25:
4-[α-(4-Cyanophenyl)-α-fluoro-5-isothiazolylmethyl]-benzonitrile 4-[α-(4-Cyanophenyl)-5-isothiazolylmethyl]-benzonitrile (Example 2) is converted into the carbanion by treatment with lithium diisopropylamide in THF at −78° and is then reacted with N-fluoro-3,3-dimethyl-2,3-dihydro-1,2-benzothiazole-1,1-dioxide. The reaction mixture is allowed to warm to room temperature and is worked up in aqueous medium, yielding the title compound.

EXAMPLE 26:
6-Cyano-1-(5-isothiazolyl)-1,2,3,4-tetrahydronaphthalene

Analogously to Example 4, 6-cyano-1-hydroxy-1-(5-isothiazolyl)-1,2,3,4-tetrahydronaphthalene (Example 15) in glacial acetic acid is convened into the title compound using tin(II) chloride and 36.5% hydrochloric acid.

EXAMPLE 27:
6-Cyano-1-fluoro-1-(5-isothiazolyl)-1,2,3,4-tetrahydronaphthalene 6-Cyano-1-(5-isothiazolyl)-1,2,3,4-tetrahydronaphthalene (Example 26) is converted into the carbanion by treatment with lithium diisopropylamide in THF at −78° and then reacted with N-fluoro-3,3-dimethyl-2,3-dihydro-1,2-benzothiazole-1,1-dioxide. The reaction mixture is allowed to warm to room temperature and is worked up in aqueous medium, yielding the title compound.

EXAMPLE 28: 10,000 tablets, each comprising 5 mg of active ingredient, for example one of the compounds prepared in Examples 1–27. are prepared:

| Composition: | |
| --- | --- |
| active ingredient | 50.00 g |
| lactose | 2535.00 g |
| corn starch | 125.00 g |
| polyethylene glycol 6000 | 150.00 g |
| magnesium stearate | 40.00 g |

| | |
|---|---|
| -continued | |
| purified water | quantum satis |

Method: All the powdered constituents are passed through a sieve having a mesh size of 0.6 mm. Then the active ingredient, the lactose, the magnesium stearate and half of the starch are mixed in a suitable mixer. The other half of the starch is suspended in 65 ml of water and the resulting suspension is added to a boiling solution of the polyethylene glycol in 260 ml of water. The paste that is formed is added to the powder mixture and granulated, if necessary with the addition of more water. The granules are dried overnight at 35° C., forced through a sieve having a mesh size of 1.2 mm and compressed to form tablets having a breaking notch.

EXAMPLE 29: 1000 capsules, each comprising 10 mg of active ingredient, for example one of the compounds prepared in Examples 1-27, are prepared:

| Composition: | |
|---|---|
| active ingredient | 10.00 g |
| lactose | 207.00 g |
| modified starch | 80.00 g |
| magnesium stearate | 3.00 g |

Method: All the powdered constituents are passed through a sieve having a mesh size of 0.6 mm. Then the active ingredient is mixed in a suitable mixer, first with the magnesium stearate and then with the lactose and the starch until the mixture is homogeneous. No. 2 hard gelatin capsules are each filled with 300 mg of the resulting mixture using a capsule-filling machine.

What is claimed is:

1. A compound of formula I

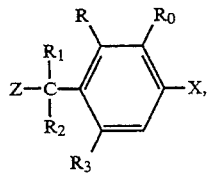

wherein Z is a five-membered nitrogen-containing heteroaromatic ring of the formula

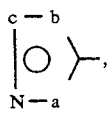

wherein one of the ring atoms a, b and c is oxygen and both of the other two ring atoms a, b and c are CH; R and $R_0$, independently of one another, are hydrogen or lower alkyl; or R and $R_0$ together are a benzo group that is unsubstituted or substituted as indicated below for aryl; $R_1$ is hydrogen, lower alkyl, hydroxy or halogen; $R_3$ is hydrogen; $R_2$ is hydrogen, lower alkyl or aryl; or $R_1$ and $R_2$ together are lower alkylidene; or $R_2$ and $R_3$ together are —$(CH_2)_2$— or —$(CH_2)_3$—; or $R_1$ and $R_2$ and $R_3$ together are a group =CH—$CH_2$— or =CH—$(CH_2)_2$—, wherein the single bond in each case is linked to the benzene ring; X is cyano, carbamoyl, N-lower alkylcarbamoyl, N,N-di-lower alkylcarbamoyl, N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl or N-hydroxycarbamoyl; and X may also be halogen, hydroxy, lower alkoxy, aryl-lower alkoxy or aryloxy when $R_2$ and $R_3$ together are —$(CH_2)_2$— or —$(CH_2)_3$— or $R_1$ and $R_2$ and $R_3$ together are a group =CH—$CH_2$— or =CH—$(CH_2)_2$—; wherein aryl is phenyl that is unsubstituted or substituted by one or more substituents from the group consisting of lower alkyl, cycloalkyl, lower alkoxy, hydroxy, lower alkanoyloxy, nitro, amino, lower alkylamino, di-lower alkylamino, halogen, trifluoromethyl, carboxy, lower alkoxycarbonyl, carbamoyl, N-lower alkylcarbamoyl, N,N-di-lower alkylcarbarmoyl, N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, cyano; N-phenyl-lower alkylcarbamoyl, N-phenylcarbamoyl, phenyl-lower alkoxy and phenoxy, each of the phenyl groups in the last four substituents mentioned being unsubstituted or substituted by lower alkyl, lower alkoxy, hydroxy, halogen or by trifluoromethyl; or a salt thereof.

2. A compound of formula I according to claim 1, wherein Z is a five-membered nitrogen-containing heteroaromatic ring selected from the group 5-isoxazolyl, 5-oxazolyl, and 4-isoxazolyl R and $R_0$ are hydrogen; or R and $R_0$ together are a benzo group that is unsubstituted or substituted by lower alkyl, lower alkoxy, hydroxy, halogen or by trifluoromethyl; $R_1$ is hydrogen, lower alkyl, hydroxy, chlorine or fluorine; $R_3$ is hydrogen; $R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; X is cyano; and X may also be halogen when $R_2$ and $R_3$ together are —$(CH_2)_3$— or $R_1$ and $R_2$ and $R_3$ together are a group =CH—$(CH_2)_2$—; or a salt thereof.

3. A compound of formula I according to claim 1, wherein Z is a five-membered nitrogen-containing heteroaromatic ring selected from the group 5-isoxazolyl, 5-oxazolyl, and 4-isoxazolyl R, $R_0$ and $R_3$ are hydrogen; $R_1$ is hydrogen, methyl, hydroxy or fluorine; $R_2$ is hydrogen, lower alkyl or cyanophenyl; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$—, the single bond being linked to the benzene ring; X is cyano; and X may also be halogen when $R_2$ and $R_3$ together are —$(CH_2)_3$— or $R_1$ and $R_2$ and $R_3$ together are a group =CH—$(CH_2)_2$—; or a salt thereof.

4. A compound of formula I according to claim 1, said compound being 4-benzonitrile.

5. A pharmaceutical composition comprising a compound according to claim 1 and at least one pharmaceutically acceptable carrier.

6. A method of using a compound according to claim 1 for the treatment of disorders which respond to inhibition of the enzyme aromatase comprising the administration of an aromatase-inhibiting effective amount of such compound to a mammal in need of such treatment.

* * * * *

UNITED STATES PATENT AND TRADEMARK OFFICE
CERTIFICATE OF CORRECTION

PATENT NO. : 5,378,721
DATED : January 3, 1995
INVENTOR(S) : Marc lang

It is certified that error appears in the above-indentified patent and that said Letters Patent is hereby corrected as shown below:

In claim 4, column 20, line 58, delete "4-benzonitrile" and insert
--4-[α-(4-cyanophenyl)-5-isoxazolylmethyl]-benzonitrile --

Signed and Sealed this

Seventh Day of March, 1995

Attest:

BRUCE LEHMAN

*Attesting Officer*          *Commissioner of Patents and Trademarks*